(12) United States Patent
Matsuo et al.

(10) Patent No.: US 7,354,911 B2
(45) Date of Patent: Apr. 8, 2008

(54) 1,3-BENZODIOXOL COMPOUND AND USE OF SAME

(75) Inventors: Noritada Matsuo, Amagasaki (JP); Hiroshi Okamoto, Ashiya (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 11/686,378

(22) Filed: Mar. 15, 2007

(65) Prior Publication Data

US 2007/0231413 A1 Oct. 4, 2007

(30) Foreign Application Priority Data

Apr. 3, 2006 (JP) ............................. 2006-101478
Dec. 27, 2006 (JP) ............................. 2006-351840

(51) Int. Cl.
*A61K 39/02* (2006.01)
*A01N 57/00* (2006.01)

(52) U.S. Cl. ........................................ 514/94; 424/339
(58) Field of Classification Search ............... 424/200, 424/339
See application file for complete search history.

(56) References Cited

OTHER PUBLICATIONS

Kuroka et al. STN Accession No. 1960:22862; Document No. 54:447d-h; Abstract of Nippon Kagaku Zasshi (1958), 79, 1554-6.*
Kuraoka, T. et al.; "Research on Safrole Derivatives (Second Report) Synthesis of 6-Propylsesamol and Its Derivatives"; J. Chem. Soc. Jpn.; 79 (12): 1544-1556 (1958).

* cited by examiner

*Primary Examiner*—D. Margaret Seaman
*Assistant Examiner*—Nizal S. Chandrakumar
(74) *Attorney, Agent, or Firm*—Panitch Schwarze Belisario & Nadel LLP

(57) ABSTRACT

Containing the 1,3-benzodioxol compound represented by the formula (I):

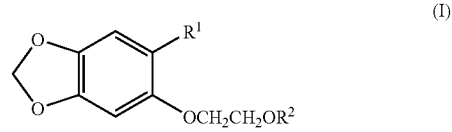

together with a pesticidal active ingredient in a pesticidal composition enhances a pest control effect of the pesticidal composition.

9 Claims, No Drawings

1,3-BENZODIOXOL COMPOUND AND USE OF SAME

BACKGROUND OF THE INVENTION

The present invention relates to 1,3-benzodioxol compound and use of the same.

In Journal of the Chemical Society of Japan, Vol. 79, No. 12, page 1554 to 1556 (December 1958), a compound enhancing a pest control effect of pesticidal compositions is described.

SUMMARY OF THE INVENTION

The present inventors have studied to find a compound having an effect of enhancing a pest control effect of a pesticidal composition in which the compound is contained together with a pesticidal active ingredient, found that a 1,3-benzodioxol compound represented by the following formula (I) has such effect, and achieved the present invention.

That is, the present invention has the following [1] to [10] aspects:

[1] A 1,3-benzodioxol compound represented by the formula (I) (hereinafter, may referred to as the present compound):

(I)

wherein $R^1$ represents C3 alkyl group or C3 alkenyl group, and $R^2$ represents C1-C3 alkyl group;

[2] The 1,3-benzodioxol compound according to [1], wherein $R^1$ is propyl group or 2-propenyl group;

[3] The 1,3-benzodioxol compound according to [1] or [2], wherein $R^1$ is methyl group.

[4] The 1,3-benzodioxol compound according to [1] or [2], wherein $R^1$ is ethyl group.

[5] The 1,3-benzodioxol compound according to [1] or [2], wherein $R^1$ is propyl group.

[6] A pesticidal composition comprising the present compound and a pesticidal active ingredient;

[7] The pesticidal composition according to [6], wherein the pesticidal active ingredient is a pyrethroid compound;

[8] A method for controlling a pest by applying an effective amount of the present compound and a pesticidal active ingredient to a pest or a biotope thereof;

[9] The method for controlling a pest according to [8], wherein the pesticidal active ingredient is a pyrethroid compound; and

[10] Use of the present compound for controlling a pest by applying to a pest or a biotope thereof together with a pesticidal active ingredient.

DETAILED DESCRIPTION OF THE INVENTION

In the present invention, examples of C3 alkyl group represented by $R^1$ include propyl group, and examples of C3 alkenyl group include 2-propenyl group.

In the present invention, examples of C1-C3 alkyl group represented by $R^2$ include methyl group, ethyl group, and propyl group.

The present compound, for example, can be produced by the following methods.

Production Method 1

The present compound can be produced, for example, by reacting the compound (II) with the compound (III):

(II)     (III)

(I)

(wherein $R^1$ and $R^2$ represent the same meaning mentioned above, and $X^1$ represents a halogen atom).

The reaction is carried out in the presence of a base, and usually in the presence of a solvent.

The solvent used for the reaction includes, for example, aliphatic hydrocarbons such as hexane and heptane; aromatic hydrocarbons such as benzene and toluene; ethers such as diethylether, tert-butylmethylether, tetrahydrofuran and 1,4-dioxane; acid amides such as N,N-dimethylformamide; sulfoxides such as dimethylsulfoxide; and water, and a mixture thereof.

The base used for the reaction includes, for example, alkali metal hydrides such as potassium hydride and sodium hydride; alkali metal hydroxides such as sodium hydroxide and potassium hydroxide; and alkali metal carbonates such as potassium carbonate and sodium carbonate. The base is used typically in a ratio of 1 to 5 moles to 1 mole of the compound (II).

The reaction may be carried out further in the co-presence of alkali metal halide. The alkali metal halide includes, for example, potassium iodide. When the alkali metal halide is co-present, it is used typically in a ratio of 1 to 5 moles to 1 mole of the compound (II).

The compound (III) is used in the reaction typically in a ratio of 1 to 5 moles to 1 mole of the compound (II).

The reaction temperature is usually in the range of 0 to 150° C., and the reaction time is usually in the range of 1 to 24 hours.

After completing the reaction, the present compound can be isolated by subjecting post treatment such as adding the reaction mixture into water, extracting with an organic solvent, and then drying and concentrating the organic layer. The present compound isolated may be further purified by chromatography and the like.

Production Method 2

The compound (I-1) of the present compound can also be produced by reducing the compound (I-2):

(I-2)

-continued (I-1)

wherein $R^2$ represents the same meaning mentioned above, and $R^{1-1}$ represents allyl group.

The reaction is carried out in the presence of hydrogen gas and a reduction catalyst, and usually in the presence of a solvent.

The solvent used for the reaction includes, for example, aliphatic hydrocarbons such as hexane and heptane; alcohols such as methanol and ethanol; esters such as ethyl acetate; and water, and a mixture thereof.

The reduction catalyst used for the reaction includes, for example, palladium carbon and platinum oxide. The reduction catalyst is used typically in a ratio of 0.05 to 0.5 moles to 1 mole of the compound (I-2).

The reaction temperature is usually in the range of 0 to 80° C., wherein the end of the reaction can be confirmed with an consumption amount of hydrogen gas theoretically required for the reduction, and the reaction time is usually in the range of 1 to 48 hours.

After completing the reaction, the compound (I-1) can be isolated by subjecting post treatment such as filtrating a reaction mixture, and then concentrating the obtained filtrate. The compound (I-1) isolated may be further purified by chromatography and the like.

Production Method 3

The present compound can be produced by reacting the compound (IV) with the compound (V):

(IV)    $X^2$—$R^2$
         (V)

(I)

wherein $R^1$ and $R^2$ represent the same meaning mentioned above, and $X^2$ represents a halogen atom.

The reaction is carried out in the presence of a base, and usually in the presence of a solvent.

The solvent used for the reaction includes, for example, aliphatic hydrocarbons such as hexane and heptane; aromatic hydrocarbons such as benzene and toluene; ethers such as diethylether, tert-butylmethylether, tetrahydrofuran, and 1,4-dioxane; acid amides such as N,N-dimethylformamide; and sulfoxides such as dimethylsulfoxide.

The base used for the reaction includes, for example, alkali metal hydrides such as potassium hydride and sodium hydride. The base is used typically in a ratio of 1 to 5 moles to 1 mole of the compound (IV).

The compound (V) is used for the reaction typically in a ratio of 1 to 5 moles to 1 mole of the compound (IV).

The reaction temperature of the reaction is usually in the range of 0 to 150° C., and a reaction time is usually in the range of 1 to 24 hours.

After completing the reaction, the present compound can be isolated by subjecting post treatment such as adding the reaction mixture into water, extracting with an organic solvent, and then drying and concentrating the organic layer. The present compound isolated may be further purified with chromatography and the like.

Referential Production Method

The compound (IV) can be produced by reacting the compound (II) with the compound (VI):

(II)    $X^3$—$CH_2CH_2OH$
        (VI)

(IV)

wherein $R^1$ represents the same meaning mentioned above, and $X^3$ represents a halogen atom.

The reaction is carried out in the presence of a base, and usually in the presence of a solvent.

The solvent used for the reaction includes, for example, aliphatic hydrocarbons such as hexane and heptane; aromatic hydrocarbons such as benzene and toluene; ethers such as diethylether, tert-butylmethylether, tetrahydrofuran, and 1,4-dioxane; acid amides such as N,N-dimethylformamide; and sulfoxides such as dimethylsulfoxide.

The base used for the reaction includes, for example, alkali metal hydrides such as potassium hydride and sodium hydride. The base is used typically in a ratio of 1 to 5 moles to 1 mole of the compound (II).

The compound (VI) is used in the reaction typically in a ratio of 1 to 5 moles to 1 mole of the compound (II).

The reaction temperature usually in the range of 0 to 150° C., and the reaction time is usually in the range of 1 to 24 hours.

After completing the reaction, the compound (IV) can be isolated by subjecting post treatment such as adding the reaction mixture into water, extracting with an organic solvent, and then drying and concentrating the organic layer. The compound (IV) isolated may be further purified with chromatography and the like.

The pesticidal composition of the present invention includes the present compound and a pesticidal active ingredient (hereinafter, the present compound and the pesticidal active ingredient being combiningly referred to as the present active ingredient). The ratio between the present compound and the pesticidal active ingredient which are contained in the pesticidal composition of the present invention is optionally adjustable without limitation according to the control objectives such as kinds of pests, places for application, timings of applying, kinds of the pesticidal active ingredient; typical weight ratio (the present compound:pesticidal active ingredient) being about 1:100 to about 100:1, preferably about 1:50 to about 50:1, more preferably 20:1 to 1:1.

Examples of the pesticidal active ingredient containing the pesticidal composition of the present invention together with the present compound include follows:

pyrethroid compounds such as allethrin, tetramethrin, prallethrin, phenothrin, resmethrin, cyphenothrin, permethrin, cypermethrin, alpha-cypermethrin, zeta-cypermethrin, deltamethrin, tralomethrin, cyfluthrin, beta-cyfluthrin, cyhalothrin, lambda-cyhalothrin, flumethrin, imiprothrin, etofenprox, fenvalerate, esfenvalerate, fenpropathrin, silafluofen, bifenthrin, transfluthrin, flucythrinate, tau-fluvalinate, acrinathrin, tefluthrin, cycloprothrin, 2,3,5,6-tetrafluoro-4-(methoxymethyl)benzyl (EZ)-(1RS, 3RS; 1RS, 3SR)-2,2-dimethyl-3-prop-1-enylcyclopropane carboxylate, 2,3,5,6-tetrafluoro-4-methylbenzyl(EZ)-(1RS, 3RS; 1RS, 3SR)-2,2-dimethyl-3-prop-1-enylcyclopropane carboxylate, 2,3,5,6-tetrafluoro-4-(methoxymethyl)benzyl (1RS, 3RS; 1RS, 3SR)-2,2-dimethyl-3-(2-methylprop-1-enyl)cyclopropanecarboxylate, empenthrin, 2,3,5,6-tetrafluoro-4-methoxymethylbenzyl(EZ)-(1RS, 3RS; 1RS, 3SR)-3-(2-cyano-1-propenyl)-2,2-dimethylcyclopropanecarboxylate, 2,3,5,6-tetrafluoro-4-methoxymethylbenzyl (EZ)-(1RS, 3RS; 1RS, 3SR)-3-(2-cyano-2-ethoxycarbonylvinyl)-2,2-dimethylcyclopropanecarboxylate, 2,3,5,6-tetrafluoro-4-methoxymethylbenzyl(1RS, 3RS; 1RS, 3SR)-3-(2,2-dichlorovinyl)-2,2-dimethylcyclopropanecarboxylate, 2,3,5,6-tetrafluoro-4-methoxymethylbenzyl(EZ)-(1RS, 3RS; 1RS, 3SR)-3-methoxyiminomethyl-2,2-dimethylcyclopropanecarboxylate and 2,3,5,6-tetrafluoro-4-methoxymethylbenzyl(EZ)-(1RS, 3RS; 1RS, 3SR)-3-(2-ethoxycarbonyl-2-fluorovinyl)-2,2-dimethylcyclopropanecarboxylate;

organic phosphorus compounds such as dichlorvos, fenitrothion, cyanophos, profenofos, sulprofos, phenthoate, isoxathion, tetrachlorvinphos, fenthion, chlorpyriphos, diazinon, acephate, terbufos, phorate, chlorethoxyfos, fosthiazate, ethoprophos, cadusafos and methidathion;

carbamate compounds such as propoxur, carbaryl, metoxadiazone, fenobucarb, methomyl, thiodicarb, alanycarb, benfuracarb, oxamyl, aldicarb and methiocarb;

benzoylphenylurea compounds such as lufenuron, chlorfluazuron, hexaflumuron, diflubenzuron, triflumuron, teflubenzuron, flufenoxuron, fluazuron, novaluron, triazuron and bistrifluron; juvenile hormone-like substances such as pyriproxyfen, methoprene, hydroprene and fenoxycarb;

neonicotinoid compounds such as acetamiprid, nitenpyram, thiacloprid, thiamethoxam, dinotefuran, imidacloprid and clothianidin;

phenylpyrazole compounds such as acetoprole and ethiprole; benzoylhydrazine compounds such as tebufenozide, chromafenozide, methoxyfenozide and halofenozide;

other pesticidal active ingredients such as diafenthiuron, pymetrozine, flonicamid, triazamate, buprofezin, spinosad, emamectin benzoate, chlorfenapyr, indoxacarb MP, pyridalyl, cyromazine, fenpyroximate, tebufenpyrad, tolfenpyrad, pyridaben, pyrimidifen, fluacrypyrim, etoxazole, fenazaquin, acequinocyl, hexythiazox, clofentezine, fenbutatin oxide, dicofol, propargite, abamectin, milbemectin, amitraz, cartap, bensultap, thiocyclam, endosulfan, spirodiclofen, spiromesifen, amidoflumet and azadirachtin.

One kind or two or more kinds of these pesticidal active ingredients may be used for the pesticidal composition of the present invention.

Although the pesticidal composition of the present invention may be the present active ingredient itself, it is usually formulated into a preparation by mixing with a solid carrier, a liquid carrier and/or a gaseous carrier and, further, if necessary, adding a surfactant and other adjuvants for formulation. That is, the pesticidal composition of the present invention usually contains the present active ingredient and further contains an inert carrier. Such a preparation includes, for example, an emulsion, an oil solution, a shampoo preparation, a flowable preparation, a powder, a wettable powder, a granule, a paste, a microcapsule, a foam, an aerosol, a carbon dioxide gas preparation, a tablet, a resin preparation, a paper preparation, a nonwoven fabric preparation, and a knitted or woven fabric preparation. These preparations may be used in the form of a poison bait, a pesticide coil, an electric pesticide mat, a smoking preparation, a fumigant, or a sheet.

A preparation of the pesticidal composition of the present invention contains usually 0.01 to 98% by weight of the present active ingredient.

A solid carrier used for formulation includes finely-divided powder or granules of clay (e.g., kaolin clay, diatomaceous earth, bentonite, Fubasami clay, acid clay, etc.), synthetic hydrated silicon oxide, talc, ceramics, other inorganic minerals (e.g., sericite, quartz, sulfur, activated carbon, calcium carbonate, hydrated silica, etc.) or chemical fertilizers (e.g., ammonium sulfate, ammonium phosphate, ammonium nitrate, ammonium chloride, urea, etc.); a substance which can be sublimated and is in the solid form at normal temperature (e.g., 2,4,6-triisopropyl-1,3,5-trioxane, naphthalene, p-dichlorobenzene, camphor, adamantan, etc.); wool; silk; cotton; hemp; pulp; synthetic resins (e.g., polyethylene resins such as low-density polyethylene, straight low-density polyethylene and high-density polyethylene; ethylene-vinyl ester copolymers such as ethylene-vinyl acetate copolymers; ethylene-methacrylic acid ester copolymers such as ethylene-methyl methacrylate copolymers and ethylene-ethyl methacrylate copolymers; ethylene-acrylic acid ester copolymers such as ethylene-methyl acrylate copolymers and ethylene-ethyl acrylate copolymers; ethylene-vinylcarboxylic acid copolymers such as ethylene-acrylic acid copolymers; ethylene-tetracyclododecene copolymers; polypropylene resins such as propylene homopolymers and propylene-ethylene copolymers; poly-4-methylpentene-1, polybutene-1, polybutadiene, polystyrene; acrylonitrile-styrene resins; styrene elastomers such as acrylonitrile-butadiene-styrene resins, styrene-conjugated diene block copolymers, and styrene-conjugated diene block copolymer hydrides; fluororesins; acrylic resins such as poly(methyl methacrylate); polyamide resins such as nylon 6 and nylon 66; polyester resins such as polyethylene terephthalate, polyethylene naphthalate, polybutylene terephthalate, and polycyclohexylenedimethylene terephthalate; polycarbonates, polyacetals, polyacrylsulfones, polyarylates, hydroxybenzoic acid polyesters, polyetherimides, polyester carbonates, polyphenylene ether resins, polyvinyl chloride, polyvinylidene chloride, polyurethane, and porous resins such as foamed polyurethane, foamed polypropylene, or foamed ethylene, etc.), glasses, metals, ceramics, fibers, cloths, knitted fabrics, sheets, papers, yarn, foam, porous substances, and multifilaments.

A liquid carrier includes, for example, aromatic or aliphatic hydrocarbons (e.g., xylene, toluene, alkylnaphthalene, phenylxylylethane, kerosine, gas oil, hexane, cyclohexane, etc.), halogenated hydrocarbons (e.g., chlorobenzene, dichloromethane, dichloroethane, trichloroethane, etc.), alcohols (e.g., methanol, ethanol, isopropyl alcohol, butanol, hexanol, benzyl alcohol, ethylene glycol, etc.), ethers (e.g., diethyl ether, ethylene glycol dimethyl ether, diethylene glycol monomethyl ether, diethylene glycol monoethyl ether, propylene glycol monomethyl ether, tetrahydrofuran, dioxane, etc.), esters (e.g., ethyl acetate, butyl acetate, etc.), ketones (e.g., acetone, methyl ethyl ketone, methyl isobutyl ketone, cyclohexanone, etc.), nitriles (e.g., acetonitrile, isobutyronitrile, etc.), sulfoxides (e.g., dimethyl sulfoxide, etc.), acid amides (e.g., N,N-dimethylformamide, N,N-dimethylacetamide, N-methylpyrrolidone, etc.), alkylidene carbonates (e.g., propylene carbonate, etc.), vegetable oil (e.g., soybean oil, cottonseed oil, etc.), vegetable essential oils (e.g., orange oil, hyssop oil, lemon oil, etc.), and water.

A gaseous carrier includes, for example, butane gas, flon gas, liquefied petroleum gas (LPG), dimethyl ether, and carbon dioxide gas.

A surfactant includes, for example, alkyl sulfate ester salts, alkyl sulfonates, alkyl aryl sulfonates, alkyl aryl ethers and polyoxyethylenated products thereof, polyethylene glycol ethers, polyvalent alcohol esters and sugar alcohol derivatives.

Other adjuvants for formulation include binders, dispersants and stabilizers, specifically, for example, casein, gelatin, polysaccharides (e.g., starch, gum arabic, cellulose derivatives, alginic acid, etc.), lignin derivatives, bentonite, sugars, synthetic water-soluble polymers (e.g., polyvinyl alcohol, polyvinylpyrrolidone, polyacrylic acid, etc.), PAP (acidic isopropyl phosphate), BHT (2,6-di-t-butyl-4-methylphenol), BHA (a mixture of 2-t-butyl-4-methoxyphenol and 3-t-butyl-4-methoxyphenol), vegetable oils, mineral oils, fatty acids and fatty acid esters.

Abase material for a resin preparation includes, for example, polyethylene resins such as low-density polyethylene, straight low-density polyethylene and high-density polyethylene; ethylene-vinyl ester copolymers such an ethylene-vinyl acetate copolymers; ethylene-methacrylic acid ester copolymers such as ethylene-methyl methacrylate copolymers and ethylene-ethyl methacrylate copolymers; ethylene-acrylic acid ester copolymers such as ethylene-methyl acrylate copolymers and ethylene-ethyl acrylate copolymers; ethylene-vinylcarboxylic acid copolymers such as ethylene-acrylic acid copolymers; ethylene-tetracyclododecene copolymers; polypropylene resins such as propylene copolymers and propylene-ethylene copolymers; poly-4-methylpentene-1, polybutene-1, polybutadiene, polystyrene, acrylonitrile-styrene resins; styrene elastomers such as acrylonitrile-butadiene-styrene resins, styrene-conjugated diene copolymers, and styrene-conjugated diene block copolymer hydrides; fluororesins; acrylic acid resins such as poly(methyl methacrylate); polyamide resins such as nylon 6 and nylon 66; polyester resins such as polyethylene terephthalate, polyethylene naphthalate, polybutylene butalate, and polycylohexylenedimethylene terephthalate; polycarbonates, polyacetals, polyacrylsulfones, polyarylate, hydroxybenzoic acid polyesters, polyetherimides, polyester carbonates, polyphenylene ether resins, polyvinyl chloride, polyvinylidene chloride, and polyurethane. These base materials may be used alone or as a mixture of two or more. A plasticizer such as phthalic acid ester (e.g., dimethyl phthalate, dioctyl phthalate, etc.), adipic acid ester or stearic acid may be added to these base materials, if necessary.

The resin preparation can be obtained by kneading the present active ingredient into the base material, followed by molding such as injection molding, extrusion molding or press molding. The resulting resin preparation may be formed into the shape of a plate, a film, a tape, a net, a string or the like via a further step of molding, cutting, or the like, if necessary. These resin preparations may be used in the form of an animal collar, an animal ear tag, a sheet preparation, a lead, or a horticultural post.

A base material of a poison bait includes, for example, cereal powder, vegetable oil, sugar and crystalline cellulose. An antioxidant such as dibutylhydroxytoluene or nordihydroguaiaretic acid, a preservative such as dehydroacetic acid, an agent for preventing children or pets from erroneously eating such as hot pepper powder, and a pest-attractive perfume such as cheese perfume, onion perfume or peanut oil may be added to the base material, if necessary.

The present compound can be used in pest control by applying an effective amount of the present compound and a pesticidal active ingredient to pests directly and/or a biotope thereof (e.g., plants, animals, soil, etc.).

When the pesticidal composition of the present invention is used for controlling pests in agriculture and forestry, the application amount is usually 1 to 100,000 g/ha, preferably 10 to 1,000 g/ha of total amount of the present active ingredient. When the pesticidal composition of the present invention is the form of an emulsion, a wettable powder, a flowable agent, or a microcapsule, it is usually used after dilution with water so as to have the present active ingredient concentration of 0.01 to 1,000 ppm. When the pesticidal composition of the present invention is the form of an oil solution, a powder or a granule, it is usually used as it is.

These preparations as it is may be sprayed as they are to plants to be protected from pests, or may be diluted with water and then sprayed to a plant to be protected from pests. Soil can be treated with these preparations to control pests living in the soil. Seedbeds before planting or planting holes or plant feet in planting can be also treated with these preparations. Further, a sheet preparation of the pesticidal composition of the present invention may be applied by winding around plants, disposing in the vicinity of plants, laying on the soil surface at the plant feet, or the like.

When the pesticidal composition of the present invention is used for a control of pests of epidemic, the application amount is usually 0.001 to 100 mg/m$^3$ of total amount of the present active ingredient for application to space, and 0.001 to 1,000 mg/m$^2$ of total amount of the present active ingredient for application to a plane. When the pesticidal composition of the present invention is the form of an emulsion, a wettable powder or a flowable agent, it is usually applied after dilution with water so as to have the present active ingredient concentration of 0.001 to 100,000 ppm, preferably 0.01 to 1,000 ppm. When the pesticidal composition of the present invention is the form of an oil solution, an aerosol, a smoking preparation or a poison bait, it is usually applied as it is. The pesticidal composition in the form of pesticide coil, or an electric pesticide mat is applied by emitting the present active ingredient by heating depending on its form. The pesticidal composition in the form of a resin preparation, a paper preparation, a tablet, a nonwoven fabric preparation, a knitted or woven fabric preparation or a sheet preparation can be applied, for example, by leaving the preparation as it is in a space to be applied and by sending air to the preparation.

A space to which the pesticidal composition of the present invention is applied for prevention of epidemics includes, for example, a closet, a Japanese-style closet, a Japanese-style chest, a cupboard, a lavatory, a bathroom, a lumber room, a living room, a dining room, a warehouse, and the car inside. The pesticidal composition may be also applied in outdoor open space.

When the pesticidal composition of the present invention is used for controlling parasites living outside of a livestock such as a cow, a horse, a pig, a sheep, a goat or a chicken, or a small animal such as a dog, a cat, a rat or a mouse, it can be used for said animal by a known method in the veterinary filed. Specifically, when systemic control is intended, the pesticidal composition is administered, for example, as a tablet, a mixture with feed, a suppository or an injection (e.g., intramuscularly, subcutaneously, intravenously, intraperitoneally, etc.). When non-systemic control is intended, a method of using the pesticidal composition of the present invention includes spraying, pour-on treatment or a spot-on treatment with the pesticidal composition in the form of an oil solution or an aqueous liquid, washing an animal with the pesticidal composition in the form of a shampoo preparation, and attachment of a collar or a ear tag made of the pesticidal composition in the form of a resin preparation to an animal. When administered to an animal, total amount of the present active ingredient is usually in the range of 0.01 to 1,000 mg per 1 kg body weight of the animal.

Pests against which the pesticidal composition of the present invention has controlling effect include harmful arthropods such as insects and mites. More specifically, examples thereof are listed below.

Hemiptera:

Delphacidae such as *Laodelphax striatellus, Nilaparvata lugens, Sogatella furcifera* and the like, Deltocephalidae such as *Nephotettix cincticeps, Nephotettix virescens* and the like, Aphididae such as *Aphis gossypii, Myzus persicae* and the like, Pentatomidae and Alydidae, such as *Nezara antennata, Riptortus clavetus, Eysarcoris lewisi, Eysarcoris parvus, Plautia stali, Halyomorpha mista* and the like, Aleyrodidae such as *Trialeurodes vaporariorum, Bemisia argentifolii* and the like, Diaspididae, Coccidae and Margarodidae, such as *Aonidiella aurantii, Comstockaspis perniciosa, Unaspis citri, Ceroplastes rubens, Icerya purchasi* and the like, Tingidae, Cimicidae such as *Cimex lectularius* and the like, Psyllidae, and the like;

Lepidoptera:

Pyralidae such as *Chilo suppressalis, Cnaphalocrocis medinalis, Notarcha derogata, Plodia interpunctella* and the like, Noctuidae such as *Spodoptera litura, Pseudaletia separata, Trichoplusia* spp., *Heliothis* spp., *Helicoverpa* spp. and the like, Pieridae such as *Pieris rapae* and the like, Tortricidae such as *Adoxophyes* spp., *Grapholita molesta, Cydia pomonella* and the like, Carposinidae such as *Carposina niponensis* and the like, Lyonetiidae such as *Lyonetia* spp. and the like, Lymantriidae such as *Lymantria* spp., *Euproctis* spp. and the like, Yponomeutidae such as *Plutella xylostella* and the like, Gelechiidae such as *Pectinophora gossypiella* and the like, Arctiidae such as *Hyphantria cunea* and the like, Tineidae such as *Tinea translucens, Tineola bisselliella* and the like;

Diptera:

Culicidae such as *Culex pipiens pallens, Culex tritaeniorhynchus, Culex quinquefasciatus* and the like,

*Aedes* spp. such as *Aedes aegypti, Aedes albopictus* and the like,

*Anopheles* spp. such as *Anopheles sinensis* and the like,

Chironomidae,

Muscidae such as *Musca domestica, Muscina stabulans* and the like,

Calliphoridae,

Sarcophagidae,

Fanniidae,

Anthomyiidae such as *Delia platura, Delia antiqua* and the like,

Tephritidae,

Drosophilidae,

Phoridae such as *Megaselia spiracularis* and the like,

Psychodidae such as *Clogmia albipunctata* and the like,

Simuliidae,

Tabanidae,

*Stomoxys* spp.,

Agromyzidae, and the like;

Coleoptera:

Corn rootworms such as *Diabrotica virgifera virgifera, Diabrotica undecimpunctata howardi* and the like, Scarabaeidae such as *Anomala cuprea, Anomala rufocuprea* and the like, Rhynchophoridae, Curculionidae and Bruchidae, such as *Sitophilus zeamais, Lissorhoptrus oryzophilus, Callosobruchus chienensis* and the like, Tenebrionidae such as *Tenebrio molitor, Tribolium castaneum* and the like, Chrysomelidae such as *Oulema oryzae, Aulacophora femoralis, Phyllotreta striolata, Leptinotarsa decemlineata* and the like, Dermestidae such as *Dermestes maculates* and the like, Anobiidae,

*Epilachna* spp. such as *Epilachna vigintioctopunctata* and the like,

Lyctidae,

Bostrychidae,

Ptinidae,

Cerambycidae,

*Paederus fuscipes*, and the like;

Blattaria: *Blattella germanica, Periplaneta fuliginosa, Periplaneta americana, Periplaneta brunnea, Blatta orientalis* and the like;

Thysanoptera: *Thrips palmi, Thrips tabaci, Frankliniella occidentalis, Frankliniella intonsa* and the like;

Hymenoptera:

Formicidae such as *Monomorium pharaosis, Formica fusca japonica, Ochetellus glaber, Pristomyrmex pungens, Pheidole noda*, and the like;

Vespidae,

Bethylidae,

Tenthredinidae such as *Athalia japonica*, and the like;

Orthoptera:

Gryllotalpidae, Acrididae, and the like;

Aphaniptera: *Ctenocephalides felis, Ctenocephalides canis, Pulex irritans, Xenopsylla cheopis*, and the like;

Anoplura: *Pediculus humanus corporis, Phthirus pubis, Haematopinus eurysternus, Dalmalinia ovis*, and the like;

Isoptera:

Subterranean termites such as *Reticulitermes speratus, Coptotermes formosanus, Reticulitermes flavipes, Reticulitermes hesperus, Reticulitermes virginicus, Reticulitermes tibialis, Heterotermes aureus*, and the like, Dry wood termites such as *Incisitermes minor*, and the like, Damp wood termites such as *Zootermopsis nevadensis*, and the like;

Acarina:

Tetranychidae such as *Tetranychus urticae, Tetranychus kanzawai, Panonychus citri, Panonychus ulmi, Oligonychus* spp. and the like, Eriophyidae such as *Aculops pelekassi, Aculus schlechtendali*, and the like, Tarsonemidae such as *Polyphagotarsonemus latus*, and the like, Tenuipalpidae, Tuckerellidae, Ixodidae such as *Haemaphysalis longicornis, Haemaphysalis flava, Dermacentor variabilis, Ixodes ovatus, Ixodes persulcatus, Ixodes scapularis, Boophilus microplus, Amblyomma americanum, Rhipicephalus sanguineus*, and the like, Acaridae such as *Tyrophagus putrescentiae*, and the like, Epidermoptidae such as *Dermatophagoides farinae, Dermatophagoides ptrenyssnus*, and the like, Cheyletidae such as *Cheyletus eruditus, Cheyletus malaccensis, Cheyletus moorei, Ornithoonyssus bacoti, Ornithonyssus sylvairum* and the like, Dermanyssidae such as *Dermanyssus gallinae*, and the like, Trombiculidae such as *Leptotrombidium akamushi*, and the like;

Araneae: *Chiracanthium japonicum, Latrodectus hasseltii*, and the like;

Chilopoda: *Thereuonema hilgendorfi, Scolopendra subspinipes*, and the like;

Diplopoda: *Oxidus gracilis, Nedyopus tambanus*, and the like;

Isopoda: *Armadillidium vulgare*, and the like;

Gastropoda: *Limax marginatus, Limax flavus*, and the like.

EXAMPLES

Next, the present invention will be specifically explained according to Examples such as Production Examples, Formulation Examples, and Test Examples, but should not be restricted thereto.

Production Examples of the present compound will be explained.

Production Example 1

After mixing 1.39 g of 5-hydroxy-6-(2-propenyl)-1,3-benzodioxol

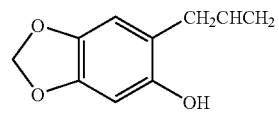

and 20 mL of anhydrous dimethylformamide, the mixture was added with 1.60 g of potassium carbonate, added with 1.14 g of 2-chloroethylmethyl ether and 0.7 g of potassium iodide under ice-cooling, and then stirred at 80° C. for 8 hours.

The reaction mixture was poured into 30 mL of ice-cooled 5% hydrochloric acid, extracted three times with 40 mL of ethyl acetate while being washed with ethyl acetate. The organic layers were combined and washed with 50 mL of saturated aqueous sodium chloride solution, dried with anhydrous magnesium sulfate, and then filtrated; and the filtrate was concentrated under reduced pressure. The residue obtained was subjected to silica-gel column chromatography to obtain 1.10 g of 5-(2-methoxyethoxy)-6-(2-propenyl)-1,3-benzodioxol (hereinafter, referred to as the present compound (1)).

The present compound (1)

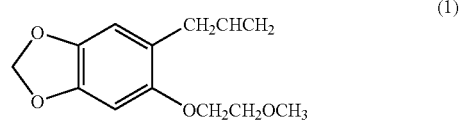

$^1$H-NMR (CDCl$_3$, TMS internal standard) δ(ppm): 3.30 (m, 2H), 3.46 (s, 3H), 3.71 (m, 2H), 4.02 (m, 2H), 5.00 (m, 2H), 5.90 (s, 1H) 2H), 5.90-5.97 (m, 1H), 6.61 (s, 1H), 6.64 (s, 1H)

Production Example 2

After mixing 0.58 g of the present compound (1) and 100 mL of ethyl acetate, the mixture was added with 40 mg of platinum oxide, and stirred under hydrogen atmosphere.

After confirming the absorption amount of hydrogen gas theoretically required for reducing 2-propenyl group of the present compound (1), the reaction mixture was filtrated. The filtrate was concentrated under reduced pressure. The residue obtained was subjected to silica-gel column chromatography to obtain 0.56 g of 5-(2-methoxyethoxy)-6-propyl-1,3-benzodioxol (hereinafter, referred to as the present compound (2)).

The present compound (2)

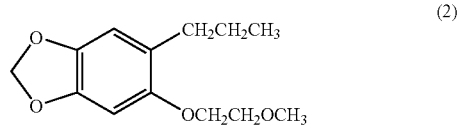

(2)

$^1$H-NMR (CDCl$_3$, TMS internal standard) δ(ppm): 0.92 (t, 3H), 1.50-1.56 (m, 2H), 2.50 (m, 2H), 3.45 (s, 3H), 3.71 (m, 2H), 4.00 (m, 2H), 5.90 (s, 2H), 6.51 (s, 1H), 6.63 (s, 1H)

Production Example 3

Except for using 2-chloroethylethyl ether in place of 2-chloroethylmethyl ether, with the same manner applied in Production Example 1, 186 mg of 5-(2-ethoxyethoxy)-6-(2-propenyl)-1,3-benzodioxol (hereinafter, referred to as the present compound (3)) was obtained.

The present compound (3)

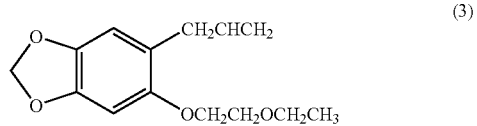

(3)

$^1$H-NMR (CDCl$_3$, TMS internal standard) δ(ppm): 1.20 (t, 3H), 3.30 (m, 2H), 3.56 (q, 2H), 3.75 (m, 2H), 4.02 (m, 2H), 5.00 (m, 2H), 5.88 (s, 2H), 5.90-5.97 (m, 1H), 6.53 (s, 1H), 6.64 (s, 1H)

Production Example 4

Except for using the present compound (3) in place of the present compound (1), with the same manner applied in Production Example 2, 160 mg of 5-(2-ethoxyethoxy)-6-propyl-1,3-benzodioxol (hereinafter, referred to as the present compound (4)) was obtained.

The present compound (4)

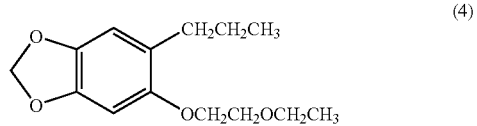

(4)

$^1$H-NMR (CDCl$_3$, TMS internal standard) δ (ppm):
0.92 (t, 3H), 1.24 (t, 3H), 1.56 (m, 2H), 2.51 (m, 2H), 3.61 (m, 2H), 3.75 (m, 2H), 4.03 (m, 2H), 5.88 (s, 2H), 6.52 (s, 1H), 6.63 (s, 1H)

Production Example 5

After mixing 5.09 g of 5-hydroxy-6-(2-propenyl)-1,3-benzodioxol and 40 mL of anhydrous dimethylformamide, the mixture was added with 4.73 g of potassium carbonate, added with 5.36 g of 2-bromoethanol under ice-cooling, and then stirred at 50° C. for 48 hours.

The reaction mixture was poured into 30 mL of ice-cooled 5% hydrochloric acid solution, extracted three times with 40 mL of ethyl acetate while being washed with ethyl acetate. The organic layers were combined and washed with 50 mL of saturated aqueous sodium chloride solution, dried with anhydrous magnesium sulfate, and then filtrated; and the filtrate obtained was concentrated under reduced pressure. The residue obtained was subjected to silica-gel column chromatography to obtain 0.53 g of 5-(2-hydroxyethoxy)-2-(2-propenyl)-1,3-benzodioxol.

5-(2-hydroxyethoxy)-2-(2-propenyl)-1,3-benzodioxol

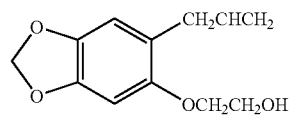

$^1$H-NMR (CDCl$_3$, TMS internal standard) δ(ppm): 2.04 (t, 1H), 3.30 (d, 2H), 3.92 (m, 2H), 4.01 (m, 2H), 5.00 (m, 2H), 5.90 (s, 2H), 5.90 (m, 1H), 6.52 (s, 1H), 6.65 (s, 1H)

After mixing 0.14 g of sodium hydride (55% mineral oil dispersion) and 10 mL of anhydrous dimethylformamide, the mixture was added under ice-cooling with a solution dissolved 0.53 g of 5-(2-hydroxyethoxy)-2-(2-propenyl)-1,3-benzodioxol in 5 mL of anhydrous dimethylformamide, added with 0.53 g of propyl iodide, and then stirred at 25° C. for 12 hours.

The reaction mixture was poured into 20 mL of ice-cooled 5% hydrochloric acid solution, extracted three times with 20 mL of ethyl acetate while being washed with ethyl acetate. The organic layers were combined and washed with 20 mL of saturated aqueous sodium chloride solution, dried with anhydrous magnesium sulfate, and then filtrated; and the filtrate was concentrated under reduced pressure. The residue obtained was subjected to silica-gel column chromatography to obtain 0.32 g of 5-{2-(propyloxy)ethoxy}-6-(2-propenyl)-1,3-benzodioxol (hereinafter, referred to as the present compound (5)).

The present compound (5)

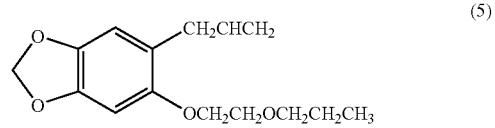

(5)

$^1$H-NMR (CDCl$_3$, TMS internal standard) δ(ppm): 0.95 (t, 3H), 1.60 (m, 2H), 3.30 (d, 2H), 3.50 (m, 2H), 3.75 (m, 2H), 4.05 (m, 2H), 5.00 (m, 2H), 5.89 (s, 2H), 5.90 (m, 1H), 6.63 (s, 1H), 6.64 (s, 1H)

Production Example 6

Except for using the present compound (5) in place of the present compound (1), with the same manner applied in Production Example 2, 192 mg of 5-{(2-propyloxy)ethoxy}-

6-propyl-1,3-benzodioxol (hereinafter, referred to as the present compound (6)) was obtained.

The present compound (6)

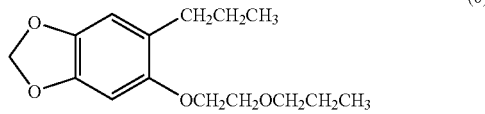

(6)

$^1$H-NMR (CDCl$_3$, TMS internal standard) δ(ppm): 0.94 (m, 6H), 1.6 (m, 4H), 2.51 (m, 2H), 3.50 (t, 2H), 3.75 (m, 2H), 4.02 (m, 2H), 5.88 (s, 2H), 6.52 (s, 1H), 6.63 (s, 1H)

The present compound will be specifically represented as follows, but the present invention should not be construed to be limited thereto.

1,3-benzodioxol compound represented by the formula (I):

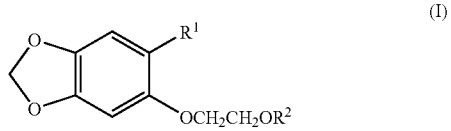

(I)

wherein R$^1$ and R$^2$ represent respective combinations listed in Table 1.

TABLE 1

| Compound Number | R$^1$ | R$^2$ |
|---|---|---|
| 1 | —CH$_2$CH=CH$_2$ | —CH$_3$ |
| 2 | —CH$_2$CH$_2$CH$_3$ | —CH$_3$ |
| 3 | —CH$_2$CH=CH$_2$ | —CH$_2$CH$_3$ |
| 4 | —CH$_2$CH$_2$CH$_3$ | —CH$_2$CH$_3$ |
| 5 | —CH$_2$CH=CH$_2$ | —CH$_2$CH$_2$CH$_3$ |
| 6 | —CH$_2$CH$_2$CH$_3$ | —CH$_2$CH$_2$CH$_3$ |
| 7 | —CH=CHCH$_3$ | —CH$_3$ |
| 8 | —CH=CHCH$_3$ | —CH$_2$CH$_3$ |
| 9 | —CH=CHCH$_3$ | —CH$_2$CH$_2$CH$_3$ |

Then, Formulation Examples will be described. The term "part" represents a part by weight. In addition, the present compound will be designated by the aforementioned compound numbers.

Formulation Example 1

Ten parts of any one of the present compounds (1) to (9) and 2 parts of permethrin are dissolved in 36 pats of xylene and 36 parts of N,N-dimethylformamide. Thereto 10 parts of polyoxyethylene styryl phenyl ether and 6 parts of calcium dodecylbenzene sulfonate are added and mixed by stirring thoroughly to obtain an emulsion.

Formulation Example 2

Ten parts of any one of the present compounds (1) to (9) and 2 parts of etofenprox are dissolved in 36 pats of xylene and 36 parts of N,N-dimethylformamide. Thereto 10 parts of polyoxyethylene styryl phenyl ether and 6 parts of calcium dodecylbenzene sulfonate are added and mixed by stirring thoroughly to obtain an emulsion.

Formulation Example 3

Five parts of SORPOL 5060 (registered trade name for TOHO Chemical Industry Co., LTD.) is added to the mixture of 40 parts of any one of the present compounds (1) to (9) and 8 parts of tetramethrin, and mixed thoroughly. Then, 28 parts of CARPLEX #80 (registered trade name for Shionogi & Co., Ltd., synthetic anhydrous silicon oxide fine powder) and 19 parts of 300 mesh diatomaceous earth are added thereto and mixed with a juice mixer to obtain a wettable powder.

Formulation Example 4

Ten parts of any one of the present compounds (1) to (9), 2 parts of phenothrin, 35 parts of white carbon containing 50 parts of polyoxyethylene alkylether sulfate ammonium salt, and 53 parts of water are mixed and then finely-divided by a wet grinding method to obtain a preparation.

Formulation Example 5

0.5 Parts of any one of the present compounds (1) to (9) and 0.1 parts of prallethrin are dissolved in 10 parts of dichloromethane. This solution is mixed with 89.4 parts of Isopar M (isoparaffin: registered trade name for Exxon Chemical) to obtain an oil solution.

Formulation Example 6

0.5 Parts of any one of the present compounds (1) to (9), 0.1 parts of cyphenothrin and 49.4 parts of NEO-THIOZOL (Chuo Kasei Co., Ltd.) are placed in an aerosol can. An aerosol valve is fitted to the can and the can is then charged with 25 parts of dimethyl ether and 25 parts of LPG. The can is shaken and an actuator is fitted to the can to obtain an oily aerosol.

Formulation Example 7

An aerosol container is charged with 3 parts of any one of the present compounds (1) to (9), 0.6 parts of imiprothrin, 0.01 part of BHT, 5 parts of xylene, a mixture of 3.39 parts of a deodorized kerosine and 1 part of an emulsifying agent [Atmos 300 (registered trade name for Atmos Chemical Ltd.)] and 47 parts of distilled water. A valve part is attached to the container and the container is then charged with 40 parts of a propellant (LPG) through the valve under pressure to obtain an aqueous aerosol.

Formulation Example 8

Three grams of any one of the present compounds (1) to (9) and 0.5 g of transfluthrin are dissolved in 20 ml of acetone and then mixed uniformly together with 96.2 g of a mosquito coil carrier [a mixture of tabu powder (powder of *Machilus thunbergii*):dregs powder (powder of parts other than the active component of pyrethrum):wood powder at a weight ratio of 4:3:3] and 0.3 g of a green pigment by stirring. Thereto 120 ml of water is added. The mixture is kneaded thoroughly, molded, and then dried to obtain a mosquito coil.

Formulation Example 9

Three grams of any one of the present compounds (1) to (9) and 0.5 g of 2,3,5,6-tetrafluoro-4-(methoxymethyl)benzyl 1R-trans-2,2-dimethyl-3-(2-methylprop-1-enyl)cyclopropanecarboxylate are dissolved in 20 ml of acetone and then mixed uniformly together with 96.2 g of a mosquito coil carrier [a mixture of tabu powder (powder of *Machilus thunbergii*):dregs powder (powder of parts other than the active component of pyrethrum):wood powder at a weight ratio of 4:3:3] and 0.3 g of a green pigment by stirring. Thereto 120 ml of water is added. The mixture is kneaded thoroughly, molded, and then dried to obtain a mosquito coil.

Formulation Example 10

Three grams of any one of the present compounds (1) to (9) and 0.5 g of 2,3,5,6-tetrafluoro-4-methoxymethylbenzyl 1R-trans-3-(1-propenyl(E/Z=1/8))-2,2-dimethylcyclopropanecarboxylate are dissolved in 20 ml of acetone and then mixed uniformly together with 96.2 g of a mosquito coil carrier [a mixture of tabu powder (powder of *Machilus thunbergii*):dregs powder (powder of parts other than the active component of pyrethrum):wood powder at a weight ratio of 4:3:3] and 0.3 g of a green pigment by stirring. Thereto 120 ml of water is added. The mixture is kneaded thoroughly, molded, and then dried to obtain a mosquito coil.

Formulation Example 11

One part of any one of the present compounds (1) to (9), 0.2 parts of d-allethrin, 0.2 parts of phenothrin and 48.6 parts of NEO-THIOZOL (Chuo Kasei Co., Ltd.) are placed in an aerosol can and an aerosol valve is fitted to the can. The can is then charged with 25 parts of dimethyl ether and 25 parts of LPG and is shaken. An actuator for a total amount spraying-type aerosol is fitted to the can obtain an aerosol.

Formulation Example 12

One part of any one of the present compounds (1) to (9), 0.2 parts of tetramethrin, 0.2 parts of permethrin and 48.6 parts of NEO-THIOZOL (Chuo Kasei Co., Ltd.) are placed in an aerosol can and an aerosol valve is fitted to the can. The can is then charged with 25 parts of dimethyl ether and 25 parts of LPG and is shaken. An actuator for a total amount spraying-type aerosol is fitted to the can obtain an aerosol.

Formulation Example 13

One part of any one of the present compounds (1) to (9), 0.2 parts of prallethrin, 0.2 parts of cyphenothrin and 48.6 parts of NEO-THIOZOL (Chuo Kasei Co., Ltd.) are placed in an aerosol can and an aerosol valve is fitted to the can. The can is then charged with 25 parts of dimethyl ether and 25 parts of LPG and is shaken. An actuator for a total amount spraying-type aerosol is fitted to the can obtain an aerosol.

Formulation Example 14

One part of any one of the present compounds (1) to (9), 0.2 parts of imiprothrin, 0.2 parts of resmethrin and 48.6 parts of NEO-THIOZOL (Chuo Kasei Co., Ltd.) are placed in an aerosol can and an aerosol valve is fitted to the can. The can is then charged with 25 parts of dimethyl ether and 25 parts of LPG and is shaken. An actuator for a total amount spraying-type aerosol is fitted to the can obtain an aerosol.

Formulation Example 15

One part of any one of the present compounds (1) to (9), 0.2 parts of 2,3,5,6-tetrafluoro-4-methoxymethylbenzyl 1R-trans-3-(1-propenyl(E/Z=1/8))-2,2-dimethylcyclopropanecarboxylate, 0.2 parts of permethrin and 48.6 parts of NEO-THIOZOL (Chuo Kasei Co., Ltd.) are placed in an aerosol can and an aerosol valve is fitted to the can. The can is then charged with 25 parts of dimethyl ether and 25 parts of LPG and is shaken. An actuator for a total amount spraying-type aerosol is fitted to the can obtain an aerosol.

Formulation Example 16

0.5 Parts of any one of the present compounds (1) to (9) and 0.1 parts of deltamethrin are dissolved in 10 parts of dichloromethane. This solution is mixed with 89.4 parts of Isopar M (isoparaffin: registered trade name for Exxon Chemical) to obtain an oil solution.

Formulation Example 17

0.5 Parts of any one of the present compounds (1) to (9) and 0.1 parts of cyhalothrin are dissolved in 10 parts of dichloromethane. This solution is mixed with 89.4 parts of Isopar M (isoparaffin: registered trade name for Exxon Chemical) to obtain an oil solution.

Formulation Example 18

0.5 Parts of any one of the present compounds (1) to (9) and 0.1 parts of fenvalerate are dissolved in 10 parts of dichloromethane. This solution is mixed with 89.4 parts of Isopar M (isoparaffin: registered trade name for Exxon Chemical) to obtain an oil solution.

Formulation Example 19

0.5 Parts of any one of the present compounds (1) to (9) and 0.1 parts of bifenthrin are dissolved in 10 parts of dichloromethane. This solution is mixed with 89.4 parts of Isopar M (isoparaffin: registered trade name for Exxon Chemical) to obtain an oil solution.

Formulation Example 20

0.5 Parts of any one of the present compounds (1) to (9) and 0.1 parts of empenthrin are dissolved in 10 parts of dichloromethane. This solution is mixed with 89.4 parts of Isopar M (isoparaffin: registered trade name for Exxon Chemical) to obtain an oil solution.

Formulation Example 21

0.5 Parts of any one of the present compounds (1) to (9) and 0.1 parts of fenitrothion are dissolved in 10 parts of dichloromethane. This solution is mixed with 89.4 parts of Isopar M (isoparaffin: registered trade name for Exxon Chemical) to obtain an oil solution.

Formulation Example 22

0.5 Parts of any one of the present compounds (1) to (9) and 0.1 parts of metoxadiazone are dissolved in 10 parts of dichloromethane. This solution is mixed with 89.4 parts of Isopar M (isoparaffin: registered trade name for Exxon Chemical) to obtain an oil solution.

Formulation Example 23

0.5 Parts of any one of the present compounds (1) to (9) and 0.1 parts of hexaflumuron are dissolved in 10 parts of dichloromethane. This solution is mixed with 89.4 parts of Isopar M (isoparaffin: registered trade name for Exxon Chemical) to obtain an oil solution.

Formulation Example 24

0.5 Parts of any one of the present compounds (1) to (9) and 0.1 parts of diflubenzuron are dissolved in 10 parts of dichloromethane. This solution is mixed with 89.4 parts of Isopar M (isoparaffin: registered trade name for Exxon Chemical) to obtain an oil solution.

Formulation Example 25

0.5 Parts of any one of the present compounds (1) to (9) and 0.1 parts of bistrifluron are dissolved in 10 parts of dichloromethane. This solution is mixed with 89.4 parts of Isopar M (isoparaffin: registered trade name for Exxon Chemical) to obtain an oil solution.

Formulation Example 26

0.5 Parts of any one of the present compounds (1) to (9) and 0.1 parts of pyriproxyfen are dissolved in 10 parts of dichloromethane. This solution is mixed with 89.4 parts of Isopar M (isoparaffin: registered trade name for Exxon Chemical) to obtain an oil solution.

Formulation Example 27

0.5 Parts of any one of the present compounds (1) to (9) and 0.1 parts of imidacloprid are dissolved in 10 parts of dichloromethane. This solution is mixed with 89.4 parts of Isopar M (isoparaffin: registered trade name for Exxon Chemical) to obtain an oil solution.

Formulation Example 28

0.5 Parts of any one of the present compounds (1) to (9) and 0.1 parts of etoxazole are dissolved in 10 parts of dichloromethane. This solution is mixed with 89.4 parts of Isopar M (isoparaffin: registered trade name for Exxon Chemical) to obtain an oil solution.

Formulation Example 29

0.5 Parts of any one of the present compounds (1) to (9) and 0.1 parts of amidoflumet are dissolved in 10 parts of dichloromethane. This solution is mixed with 89.4 parts of Isopar M (isoparaffin: registered trade name for Exxon Chemical) to obtain an oil solution.

The following Test Example exhibits the effectiveness of the pesticidal composition containing the present compound and a pesticidal active ingredient, for controlling pests. The present compounds are represented by the compound numbers defined above.

Test Example

After mixing the present compounds (1), (2), (3), (4), (5), and (6) with d-allethrin respectively, acetone solutions containing each mixture with the respective prescribed concentrations (w/v) listed in Table 2 were prepared. A female adult *Musca domestica* was applied with 0.5 µL of the acetone solution dropped on the back side of its chest region, transferred to a plastic cup having about 9 cm diameter and about 4.5 cm height, and then left at 25° C. with being fed by 5% of aqueous sugar solution. After 24 hours, live and death of the *Musca domestica* was observed to obtain a mortality ratio. The number of the *Musca domesticas* contained in each cup was 10, and the test was repeated twice.

Furthermore, after preparing acetone solutions containing each of the present compounds (1), (2), (3), (4), (5), and (6) and d-allethrin in the respective prescribed concentrations (w/v) listed in Table 2, a test was conducted as the same manner mentioned above.

For comparison, with using 4,5-methylenedioxy-2-propylphenyl2-butoxyethyl ether (hereinafter, referred to as a comparative compound)

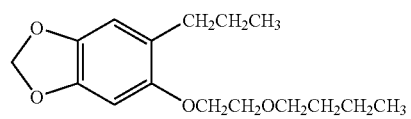

in place of the present compounds, a test was conducted in the same manner. The results are shown in Table 2.

TABLE 2

| Test compound | Concentration of test compound [% (w/v)] | Concentration of d-allethrin [% (w/v)] | mortality ratio [%] |
|---|---|---|---|
| The present compound (1) | 1.25 | 0 | 0 |
|  | 1.25 | 0.25 | 100 |
| The present compound (2) | 1.25 | 0 | 0 |
|  | 1.25 | 0.25 | 90 |
| The present compound (3) | 1.25 | 0 | 0 |
|  | 1.25 | 0.25 | 100 |
| The present compound (4) | 1.25 | 0 | 0 |
|  | 1.25 | 0.25 | 100 |
| The present compound (5) | 1.25 | 0 | 0 |
|  | 1.25 | 0.25 | 90 |
| The present compound (6) | 1.25 | 0 | 0 |
|  | 1.25 | 0.25 | 80 |
| Comparative compound | 1.25 | 0 | 0 |
|  | 1.25 | 0.25 | 55 |
| None (d-allethrin) | — | 0.25 | 0 |

Containing the present compound together with a pesticidal active ingredient in a pesticidal composition enhances a pest control effect of the pesticidal composition.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

The invention claimed is:

1. A 1,3-benzodioxol compound represented by the formula (I):

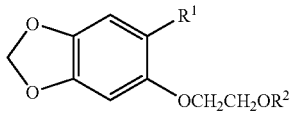

(I)

wherein R¹ represents C3 alkyl group or C3 alkenyl group, and R² represents C1-C3 alkyl group.

2. The 1,3-benzodioxol compound according to claim 1, wherein R¹ is propyl group or 2-propenyl group.

3. The 1,3-benzodioxol compound according to claim 1, wherein R² is methyl group.

4. The 1,3-benzodioxol compound according to claim 1, wherein R² is ethyl group.

5. The 1,3-benzodioxol compound according to claim 1, wherein R² is propyl group.

6. A pesticidal composition comprising a 1,3-benzodioxol compound represented by the formula (I):

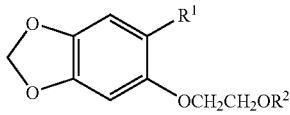

(I)

wherein R¹ represents C3 alkyl group or C3 alkenyl group, and R² represents C1-C3 alkyl group;

and a pesticidal active ingredient.

7. The pesticidal composition according to claim 6, wherein the pesticidal active ingredient is a pyrethroid compound.

8. A method for controlling a pest by applying an effective amount of a 1,3-benzodioxol compound represented by the formula (I):

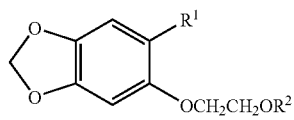

(I)

wherein R¹ represents C3 alkyl group or C3 alkenyl group, and R² represents C1-C3 alkyl group;

and a pesticidal active ingredient to a pest or a biotope thereof.

9. The method for controlling a pest according to claim 8, wherein the pesticidal active ingredient is a pyrethroid compound.

* * * * *